United States Patent [19]

Cheminal et al.

[11] Patent Number: 5,731,481
[45] Date of Patent: Mar. 24, 1998

[54] PROCESS FOR THE MANUFACTURE OF 1,1,1,2-TETRAFLUOROETHANE

[75] Inventors: Bernard Cheminal, Brignais; Eric Lacroix, Lyons; Andre Lantz, Vernaison, all of France

[73] Assignee: Societe Atochem, France

[21] Appl. No.: 772,521

[22] Filed: Dec. 24, 1996

Related U.S. Application Data

[63] Continuation of Ser. No. 445,862, May 22, 1995, abandoned, which is a continuation of Ser. No. 297,536, Aug. 31, 1994, abandoned, which is a continuation of Ser. No. 46,348, Apr. 9, 1993, abandoned, which is a continuation of Ser. No. 790,059, Nov. 12, 1991, abandoned.

[51] Int. Cl.$^6$ .................................................. C07C 17/08
[52] U.S. Cl. ........................................ 570/168; 570/169
[58] Field of Search ................................ 570/168, 169

[56] References Cited

U.S. PATENT DOCUMENTS

| | | |
|---|---|---|
| 3,650,937 | 3/1972 | Henig . |
| 3,787,331 | 1/1974 | Groppelli et al. . |
| 3,793,229 | 2/1974 | Groppelli et al. ............... 570/168 |
| 4,129,603 | 12/1978 | Bell ............................. 570/169 |
| 4,147,733 | 4/1979 | Fiske et al. ..................... 570/168 |
| 4,922,037 | 5/1990 | Manzer ........................... 570/168 |

FOREIGN PATENT DOCUMENTS

| | | |
|---|---|---|
| 4943922 | 12/1970 | Japan ............................ 570/169 |
| 2-172933/90 | 7/1990 | Japan . |
| 90/08755 | 9/1990 | WIPO . |

*Primary Examiner*—Alan Siegel
*Attorney, Agent, or Firm*—Bell, Boyd & Lloyd

[57] ABSTRACT

The invention relates to the manufacture of 1,1,1,2-tetrafluoroethane (F134a) by gas-phase catalytic fluorination of 1-chloro-2,2,2-trifluoroethane (F133a).

A mixed catalyst is employed, composed of nickel and chromium oxides, halides and/or oxyhalides deposited on a support consisting of aluminium fluoride or of a mixture of aluminium fluoride and alumina.

This mixed catalyst makes it possible to obtain an excellent selectivity for F134a with a high production efficiency.

21 Claims, No Drawings

PROCESS FOR THE MANUFACTURE OF 1,1,1,2-TETRAFLUOROETHANE

This is a continuation of application Ser. No. 08/445,862, filed on May 22, 1995, now abandoned; which is a continuation of application Ser. No. 08/297,536 filed Aug. 31, 1994; which is a continuation of application Ser. No. 08/046,348 filed Apr. 9, 1993; which is a continuation of application Ser. No. 07/790,059 filed Nov. 12, 1991, all abandoned.

FIELD OF THE INVENTION

The present invention relates to the manufacture of 1,1,1,2-tetrafluoroethane by gas-phase catalytic fluorination of 1-chloro-2,2,2-trifluoroethane with the aid of hydrofluoric acid.

BACKGROUND OF THE INVENTION 1,1,1,2-Tetrafluoroethane (known in the art under the designation F134a) is a compound of potential interest for replacing dichlorodifluoromethane (F12) employed currently as a refrigerant fluid, but suspected of contributing to the weakening of the stratospheric ozone layer. Economical processes for producing F134a on an industrial scale are therefore currently under investigation, one of these being the fluorination of 1-chloro-2,2,2-trifluoroethane (known in the art under the designation F133a).

Gas-phase catalytic fluorination of chlorinated or brominated hydrocarbons by means of hydrofluoric acid is a known method of gaining access to fluorinated hydrocarbons.

Thus, in U.S. Pat. No. 2,744,147, there is a description of an alumina-based catalyst promoted by a metal (cobalt, nickel or chromium) and its use in a fluidized bed for the fluorination of haloalkanes at a temperature of between 180° and 425° C. This patent addresses more especially the fluorination of haloalkanes containing 1 or 2 carbon atoms at least one of which carries at least two halogen atoms which have an atomic number not exceeding 35, at least one of these halogen atoms being chlorine or bromine.

The same applies to U.S. Pat. No. 2,744,148, which describes an alumina-based catalyst promoted by a metal (chromium, cobalt, nickel, copper or palladium) and its use for the fluorination of haloalkanes to highly fluorinated products. This patent also describes a process for activating the catalyst and converting a part of the alumina to basic aluminium fluorides.

No indication is given in these U.S. patents with regard to the working life of these catalytic formulations. In addition, no example describes the fluorination of 1-chloro-2,2,2-trifluoroethane, a fluorination which exhibits the special feature of being an equilibrium reaction resulting in partial conversions of the raw material and in which, furthermore, the formation of unsaturated compounds gives rise to phenomena of fouling of the catalysts owing to coke deposition, which is detrimental to their lifetime.

U.S. Pat. No. 3,514,253 describes aluminium fluoride-based catalysts impregnated with copper, cobalt, chromium or nickel salts and their use in the fluorination of aromatic (trichlorobenzene) or cyclic (octachlorocyclopentene) compounds.

The fluorination process described in U.S. Pat. No. 4,147,733 for the manufacture of 1,1,1-trifluoroethane or difluoromethane in the presence of aluminium, chromium and/or nickel fluorides is characterized in that steam is added to the reactants. This process does not apply to 1,1,1,2-tetrafluoroethane, whose chloro precursor (1-chloro-2,2,2-trifluoroethane) can react with water under the operating conditions which are described.

Patent FR 2,014,711 claims a process for the fluorination of haloalkanes, most especially that of 1,1,2-trichloro-1,2,2-trifluoroethane to symmetrical 1,2-dichloro 1,1,2,2-tetrafluoroethane with the aid of a catalyst consisting of aluminium fluoride and of small quantities of iron, chromium and optionally nickel compounds; this catalyst is also suitable for the chlorofluorination of ethylene. In the first reaction the $NiF_2/AlF_3$ catalyst turns out to be more active than the mixed catalyst: ($NiF_2$+$CrF_3$(see Tests no. 2 and 6 of Table 1 on page 9). For the same type of fluorination, U.S. Pat. No. 3,793,229 describes the use of $AlF_3$-supported zinc, chromium and nickel catalysts, and U.S. Pat. No. 3,787,331 that of $AlF_3$-supported manganese, chromium and optionally nickel catalysts. None of these three patents mentions the fluorination reaction of 1-chloro-2,2,2-trifluoroethane.

Patent Application WO 89/10,341 claims a process for the fluorination of saturated or unsaturated compounds in the presence of a catalyst based on very pure alumina (containing less than 100 ppm of sodium, and porous) used as a support for metal (nickel, cobalt, iron, manganese, chromium, copper or silver) fluorides. This technique, which requires a high-purity catalyst, results, in particular, in selectivities for 1,1,1,2-tetrafluoroethane which are high but frequently lower than 97.5% and to a production efficiency which is frequently lower than 65 g/hour per liter of catalyst.

In Patent SU 466,202 there is a description of a method of fluorination of vinyl chloride in the presence of a catalyst consisting of aluminium fluoride, nickel fluoride and chromium oxide. No reference is made to the preparation of the catalyst, to its lifetime or, above all, to its activity in the synthesis of 1,1,1,2-tetrafluoroethane.

Patent Applications EP 0,328,127 and 0,331,991 refer specifically to the manufacture of 1,1,1,2-tetrafluoroethane by gas-phase catalytic fluorination of 1-chloro-2,2,2-trifluoroethane with the aid of hydrofluoric acid. According to Document EP 0,328,127 the operation is carried out in the presence of oxygen and employs a catalyst containing a metal chosen from the group consisting of Co, Mn, Ni, Pd, Ag and Ru on an aluminium fluoride support. In the process of Document EP 0,331,991 a catalyst is employed, containing a metal of groups VIII, VIIB, IIIB, IB or a metal which has an atomic number from 58 to 71 on an aluminium fluoride or charcoal support. Example 5 of the latter document shows that, with a nickel catalyst at 350° C. with a contact time of 30 seconds and an HF/F133a molar ratio of 10, the F133a conversion is only 8% and the selectivity for F134a is only 86.3%; an increase in temperature (400° and 425° C. in Examples 6 and 7) improves the F133a conversion but does not appreciably alter the selectivity for F134a, which remains at approximately 85%.

It has now been found that a very high selectivity for F134a (close to 100%) can be obtained by employing a mixed catalyst based on nickel and chromium.

DESCRIPTION OF THE INVENTION

The subject of the invention is therefore a process for the manufacture of 1,1,1,2-tetrafluoroethane (F134a) by gas-phase catalytic fluorination of 1-chloro-2,2,2-trifluoroethane (F133a) with the aid of hydrofluoric acid, characterized in that a mixed catalyst is employed, composed of nickel and chromium oxides, halides and/or oxyhalides deposited on a support consisting of aluminium fluoride or of a mixture of aluminium fluoride and alumina.

This catalyst can be prepared in a manner which is known per se from an activated alumina. In a first stage the latter may be converted to aluminium fluoride or to a mixture of aluminium fluoride and of alumina by fluorination with the aid of air and hydrofluoric acid, the degree of conversion of alumina to aluminium fluoride depending essentially on the temperature at which the fluorination of alumina is performed (in general between 200° and 450° C., preferably between 250° and 400° C.). The support is then impregnated with the aid of aqueous solutions of chromium and nickel salts or with the aid of aqueous solutions of chromic acid. Of nickel salt and of methanol (used as a reducing agent for chromium).

Chlorides are preferably employed as chromium and nickel salts, but it is also possible to employ other salts, such as, for example, oxalates, formates, acetates, nitrates and sulphates or nickel dichromate, provided that these salts are soluble in the quantity of water capable of being absorbed by the support.

The catalyst employed in the process according to the invention can also be prepared by impregnating activated alumina directly with the aid of solutions of the abovementioned chromium and nickel compounds. In this case the conversion of at least a proportion (70% or more) of the alumina to aluminium fluoride takes place during the catalyst activation stage.

The activated aluminas to be employed for the preparation of the catalyst according to the present invention are well-known products which are available commercially. They are generally prepared by calcining alumina hydrates at a temperature of between 300° and 800° C. The activated aluminas which can be employed within the scope of the present invention may have high sodium contents (up to 1000 ppm) without this being detrimental to their performance in catalysis.

The catalyst according to the invention may contain from 0.5 to 20% of chromium and from 0.5 to 20% of nickel by weight and, preferably, between 2 and 10% of each of the metals in a nickel/chromium atomic ratio of between 0.5 and 5, preferably close to 1.

Before being capable of catalyzing the reaction of fluorination of F133a to F134a, the catalyst according to the invention must be conditioned, that is to say converted to constituents which are active and stable (under reaction conditions), by a preliminary operation known as activation.

This treatment may be carried out either in situ (in the fluorination reactor) or else in a suitable apparatus designed to withstand the conditions of activation. The latter generally comprises the following stages:

drying at low temperature (100° to 150° C., preferably 110° to 120° C.) in the presence of air or nitrogen, drying at high temperature (350° to 450° C., preferably 390° to 410° C.) under nitrogen, fluorination at low temperature (180° to 300° C., preferably at approximately 200° C.) by means of a mixture of hydrofluoric acid and nitrogen, the HF content being controlled so that the temperature does not exceed 300° C., and finishing under a stream of pure hydrofluoric acid at a temperature which can go up to 450° C.

During this operation the catalyst precursors (nickel and chromium halides, nickel chromate or dichromate, chromium oxide) are convened to the corresponding fluorides and/or oxyfluorides, which results in a release of water and/or hydrochloric acid.

After this activation the chemical analysis of the elements (chromium, nickel, fluorine, aluminium, oxygen) allows the inorganic composition of the catalyst according to the invention to be verified.

The operating conditions for the synthesis of 1,1,1,2-tetrafluoroerhane ( F134a ) by gas-phase fluorination of 1-chloro-2,2,2-trifluoroethane (F133a) with the aid of hydrofluoric acid in the presence of the catalyst according to the invention are as follows:

a) The catalyst can function either in a fluidized bed or in a stationary bed. The second method of operation is preferred because the reaction is found to be virtually athermic.

b) The reaction temperature depends on the operating pressure. At atmospheric pressure the reaction temperature is between 300° and 375° C. and preferably between 330° and 360° C.; at higher pressure (at about 15 bars absolute) the optimum temperature is between 350° and 420° C. and preferably between 375° and 410° C.

c) The HF/F 133a molar ratio may vary between 1 and 20, but preferably between 2 and 5.

d) The contact time, calculated as the flow time of the gases (under reaction conditions) through the bulk catalyst volume, is between 2 and 30 seconds. It is preferably between 3 and 5 seconds at atmospheric pressure and between 5 and 25 seconds at higher pressure (at about 15 bars absolute).

e) The addition of oxygen to maintain the catalyst activity is not obligatory and depends upon the operating conditions of the catalyst. Under conditions yielding the highest productivity and when a life duration is desired which is compatible with an industrial working, the continuous or discontinuous regeneration of the catalyst can be carried out in the presence of oxygen; its concentration in the gases (reactants or inert) should be sufficient to cause the burning of the carbonaceous products which are responsible for the deactivation.

f) The operating pressure is between 1 and 20 bars absolute, preferably between 12 and 16 bars absolute.

The following examples illustrate the invention without limiting it.

EXAMPLES

EXAMPLE 1

1A—CATALYST PREPARATION AND ACTIVATION

In a rotary evaporator are placed 250 ml of a support containing 73% of aluminium fluoride and 27% of alumina by weight, obtained in a preceding stage by fluorination of Grace HSA alumina in a fluidized bed at about 300° C. with the aid of air and hydrofluoric acid (from 5 to 10% concentration by volume of this acid in air). The initial Grace HSA alumina has the following physicochemical characteristics:

form: 1–2 mm diameter beads
BET surface area: 223 m$^2$/g
pore volume: 1.2 cm$^2$/g (for pore radii of between 40 Å and 63 microns)
sodium content: 990 ppm Two separate aqueous solutions are prepared independently:

a) chromic solution with the addition of nickel chloride, containing:
   chromic anhydride: 12.5 g
   nickel chloride hexahydrate: 29 g
   water: 40 g b) methanol solution containing:
   methanol: 17.8 g
   water: 50 g The mixture of these two solutions is then introduced onto the stirred support at room temperature, at atmospheric pressure and over approximately 45 minutes. The catalyst is then dried in a stream of nitrogen, in a fluidized bed, for 4 hours at about 110° C.

100 ml (72 g) of dry catalyst are charged into a tubular reactor made of Inconel of 27-mm internal diameter and the temperature is raised to 120° C. under a stream of nitrogen at atmospheric pressure. This treatment is continued for 15 hours and the nitrogen is then replaced with air at the same temperature for 4 hours. The temperature is then raised to 400° C. under a stream of nitrogen and is then maintained for 14 hours (heating period included).

The temperature is then returned to 200° C. under a stream of nitrogen for 15 hours and the nitrogen is then gradually replaced with hydrofluoric acid, care being taken that the temperature increase does not exceed 95° C.

The temperature is finally raised to 450° C. under a stream of pure hydrofluoric acid (1 mole/hour) for 6 hours.

A final descent back to 350° C. then takes place (under a stream of nitrogen) to start the catalysis test. The physical chemical properties of the catalyst dried and activated in this way are as follows:
chemical composition (by weight)
fluorine 61.6% ($\geq$95% $AlF_3$)
aluminium 27.5%
nickel 3.6%
chromium 2.9%
oxygen 4.4%
physical properties
BET surface area: 15.9 $m^2/g$
volume of the pores with a radius of between 40 Å and 63 microns: 0.430 $cm^3/g$
surface area of the pores with a radius greater than 40 Å: 16.0 $m^2/g$
surface area of the pores with a radius greater than 250 Å: 6.1 $m^2/g$
surface area of the pores with a radius of between 50 and 250 Å: 6.1 $m^2/g$ 1B—FLUORINATION OF F133a TO F134a The performance of the catalyst was tested under the following operating conditions, without oxygen addition:
catalyst volume (in bulk): 75 ml
temperature: 350° C.
pressure: atmospheric
hydrofluoric acid flow rate: 1.09 moles/h
F133a flow rate: 0.26 moles/h
that is to say an HF/F 133a molar ratio=4.2 ±0.3 and a contact time of 3.9±0.2 seconds under the reaction conditions.

The gases resulting from the reaction are freed from hydrogen acids by washing with water and are then dried and analyzed by V.P.C.

The main results obtain during a test of 402 hours of continuous operation on this same catalyst charge are collected in Table 1 below.

TABLE 1

| Cumulative operating time (hours) | RESULTS OBTAINED | | |
|---|---|---|---|
| | F133a conversion (%) | Selectivity for F134a (%) | Production efficiency for F134a (grams/hour per liter of catalyst) |
| 42 | 20.4 | 99.0 | 75 |
| 114 | 21.0 | 99.0 | 76 |

TABLE 1-continued

| Cumulative operating time (hours) | RESULTS OBTAINED | | |
|---|---|---|---|
| | F133a conversion (%) | Selectivity for F134a (%) | Production efficiency for F134a (grams/hour per liter of catalyst) |
| 228 | 21.0 | 98.6 | 73 |
| 282 | 21.1 | 98.6 | 71 |
| 348 | 20.9 | 99.0 | 75 |
| 402 | 21.5 | 99.1 | 76 |

EXAMPLE 2

2A—CATALYST PREPARATION AND ACTIVATION

The operation is carried out as in Example 1A, but with the chromic anhydride replaced with chromium trichloride hexahydrate and leaving out the methanol.

A single aqueous solution is prepared, containing:
chromium trichloride hexahydrate: 33.3 g
nickel chloride hexahydrate: 29 g
water: 112 g
and 250 ml of the same support are impregnated with this solution for one hour.

The remainder of the drying and activation treatment is identical with that described in Example 1A.

The chemical composition by weight of the activated catalyst is as follows:
fluorine: 61.9%
aluminium: 27.9%
nickel: 3.6%
chromium: 3%
oxygen: 3.6%

Its physical properties are as follows:
BET surface area: 36.1 $m^2/g$
volume of the pores with a radius of between 40 Å and 63 microns: 0.441 $cm^3/g$
surface area of the pores with a radius greater than 40 Å: 35.5 $m^2/g$
surface area of the pores with a radius greater than 250 Å: 4.3 $m^2/g$
surface area of the pores with a radius of between 50 and 250 Å: 20.1 $m^2/g$ 2B—FLUORINATION OF F133a TO F134a This catalyst was tested in operating conditions which were the same as those described in Example 1B. The results obtained during a test of 123 hours of continuous operation, without oxygen addition, are collected in Table 2 below.

TABLE 2

| Cumulative operating time (hours) | RESULTS OBTAINED | | |
|---|---|---|---|
| | F133a conversion (%) | Selectivity for F134a (%) | Production efficiency for F134a (grams/hour per liter of catalyst) |
| 23 | 21.2 | 98.6 | 73 |
| 41 | 20.8 | 98.6 | 75 |
| 58 | 20.9 | 98.6 | 75 |
| 123 | 20.4 | 98.5 | 73 |

EXAMPLE 3
(comparative)—CATALYST CONTAINING CHROMIUM WITHOUT NICKEL

The catalyst was prepared and activated by operating exactly as described in Example 1A, but leaving out the 29 g of nickel chloride hexahydrate in the aqueous solution a).

The chemical composition of the activated catalyst is as follows:
fluorine: 63.3%
aluminium: 30.1%
chromium: 3.5%
oxygen: 3.1%

Its physical properties are as follows:
BET surface area: 18.6 m$^2$/g
volume of the pores with a radius of between 40 Å and 63 microns: 0.438 cm$^3$/g
surface area of the pores with a radius greater than 40 Å: 21.3 m$^2$/g
surface area of the pores with a radius greater than 250 Å: 5.9 m$^2$/g
surface area of the pores with a radius of between 50 and 250 Å: 9.8 m$^2$/g This catalyst was tested in the same operating conditions as those described in Example 1B. The results obtained during a test of 126 hours' continuous running, without oxygen addition, are assembled in Table 3 below.

TABLE 3

| | | RESULTS OBTAINED | |
|---|---|---|---|
| Cumulative operating time (hours) | F133a conversion (%) | Selectivity for F134a (%) | Production efficiency for F134a (grams/hour per liter of catalyst) |
| 24 | 20.4 | 98.0 | 72 |
| 48 | 18.1 | 98.3 | 64 |
| 73 | 17.9 | 98.9 | 63 |
| 98 | 16.9 | 98.8 | 60 |
| 126 | 15.5 | 96.1 | 54 |

The comparison of these results with those of Tables 1 and 2 makes it possible to conclude that the nickel-chromium combination according to the invention is more active and, above all, more stable with time.

EXAMPLE 4
4A—CATALYST PREPARATION AND ACTIVATION

The operation is carried out as in Example 1A with the same support, but modifying the contents of the two aqueous solutions as follows:

a) chromic solution of nickel chloride, containing:
chromic anhydride: 25 g
nickel chloride hexahydrate: 58 g
water: 40 g b) methanol solution containing:
methanol: 35.6 g
water: 30 g Drying and activation of the catalyst were performed exactly as indicated in Example 1A.

The chemical composition and physical properties of the catalyst thus obtained are as follows:
chemical composition (by weight)
fluorine: 58.4%
aluminium: 24.6%
nickel: 6.8%
chromium: 5.1%
oxygen: 5.1%
physical properties:
BET surface area: 15.1 m$^2$/g
Volume of the pores with a radius of between 40 Å and 63 microns: 0.382 cm$^3$/g
Surface area of the pores with a radius greater than 40 Å: 20 m$^2$/g
Surface area of the pores with a radius greater than 250 Å: 7.7 m$^2$/g
Surfaces area of the pores with a radius of between 50 and 250 Å: 8.2 m$^2$/g

4B—FLUORINATION OF F133a TO F134a

The performance of the catalyst was tested under the following operating conditions:
catalyst volume (in bulk): 175 ml
temperature: 350° C.
pressure (absolute): 12 bars
hydrofluoric acid flow rate: 5.35 moles/h
F133a flow rate: 2.67 moles/h An HF/F133a molar ratio comprised between 2 and 2.4 and a contact time comprised between 16.5 and 17.9 seconds were maintained during the test.

The gases resulting from the reaction are relieved to atmospheric pressure, then freed from hydrogen acids by washing with water, and are then dried and analysed by V.P.C.

The main results obtained during a test of 54 hours of continuous operation on this same catalyst charge are collected in Table 4 below.

TABLE 4

| | | RESULTS OBTAINED | |
|---|---|---|---|
| Cumulative operating time (hours) | F133a conversion (%) | Selectivity for F 134a (%) | Production efficiency for F134a (grams/hour per liter of catalyst) |
| 12.5 | 13.8 | 97.3 | 205 |
| 29.5 | 13.4 | 97.4 | 210 |
| 36.5 | 13.3 | 97.2 | 206 |
| 53.5 | 13.3 | 97.4 | 210 |

We claim:

1. Process for the selective manufacture of 1,1,1,2-tetrafluoroethane (F134a) by catalytic fluorination of 1-chloro-2,2,2-trifluoroethane with the aid of gaseous hydrofluoric acid comprising employing a mixed catalyst consisting of nickel and chromium oxides, halides and/or oxyhalides deposited by impregnation on a support consisting of aluminum fluoride or a mixture of aluminum fluoride and alumina.

2. Process according to claim 1, wherein the weight content of nickel and chromium in the catalyst is between 0.5 and 20% for each metal, the nickel/chromium atomic ratio being between 0.5 and 5.

3. Process according to claim 1, wherein the support contains up to 1000 ppm of sodium.

4. Process according to claim 1, wherein the reaction temperature is between 300° and 420° C.

5. Process according to claim 1, wherein the operating pressure is between 1 and 20 bars absolute.

6. Process according to claim 1, wherein the HF/F 133a molar ratio is between 1 and 20.

7. Process according to claim 1, wherein the contact time, calculated under the reaction conditions, is between 2 and 30 seconds.

8. Process according to claim 2, wherein the nickel/chromium atomic ratio is about 1.

9. Process according to claim, 4, wherein the reaction temperature is between 330° and 410° C.

10. Process according to claim 5, wherein the operating pressure is between 12 and 16 bars.

11. Process according to claim 6, wherein the molar ratio is between 2 and 5.

12. Process according to claim 7, wherein the contact time is between 5 and 25 seconds.

13. Process for the selective manufacture of 1,1,1,2-tetrafluoroethane by catalytic fluorination of 1-chloro-2,2,2-trifluoroethane with the aid of gaseous hydrofluoric acid comprising employing a mixed catalyst consisting of nickel and chromium compounds in the form of oxides, halides and/or oxyhalides, deposited by impregnation on a support consisting of aluminum fluoride or a mixture of aluminum fluoride and alumina, wherein the content of nickel and chromium in the catalyst is between 0.5 and 20% by weight for each metal and wherein the nickel/chromium atomic ratio is between 0.5 and 5.

14. Process for the manufacture of 1,1,1,2-tetrafluoroethane by catalytic fluorination of 1-chloro-2,2,2-trifluoroethane in the presence of gaseous hydrofluoric acid comprising employing a mixed catalyst consisting essentially of nickel and of chromium compounds in the form of oxides, halides and/or oxyhalides, deposited on a support consisting of aluminum fluoride or a mixture of aluminum fluoride and alumina, wherein (a) said nickel and chromium compounds are deposited on said support by impregnation, (b) the content of nickel and chromium in the catalyst is between 0.5 and 20% by weight for each metal and (c) the nickel/chromium atomic ratio is between 0.5 and 5.

15. The process of claim 13 wherein the content of nickel and chromium in the catalyst is between 2% and 10% by weight for each metal.

16. The process of claim 13 wherein impregnation includes:

(a) said support being combined with an aqueous solution of chromic acid and a nickel salt, and said chromic acid being reduced; or (b) said support being combined with an aqueous solution of chromium and nickel salts.

17. The process of claim 13 wherein selectivity for said 1,1,1,2-tetrafluoroethane is at least 97.2%.

18. The process of claim 13 wherein selectivity for said 1,1,1,2-tetrafluoroethane is about 98.5%.

19. The process of claim 18 wherein conversion of said 1-chloro-2,2,2-trifluoroethane is about 20 4% and wherein selectivity for said 1,1,1,2-tetrafluoroethane is about 98.5%.

20. The process of claim 13 wherein the catalytic fluorination is carried out at a temperature of between 300° and 420° C., a pressure of between 1.0 and 20 bars, a contact time of between 2.0 and 30 seconds and a hydrofluoric acid/1-chloro-2,2,2-trifluoroethane molar ratio of between 1.0 and 20.

21. The process of claim 13 wherein the catalytic fluorination is carried out at a temperature of between 300° and 420° C., a pressure of between 1.0 and 20 bars, a contact time of between 2.0 and 30 seconds and a hydrofluoric acid/1-chloro-2,2,2-trifluoroethane molar ratio of between 1.0 and 20; and wherein, for at least 400 hours, conversion of said 1-chloro-2,2,2-trifluoroethane is at least 20.4%, selectively for said 1,1,1,2-tetrafluoroethane is at least 98.5%, and production efficiency for 1,1,1,2-tetrafluoroethane is at least 71 grams per hour per liter of said catalyst.

* * * * *